(12) United States Patent
Mleczko et al.

(10) Patent No.: US 10,105,675 B2
(45) Date of Patent: Oct. 23, 2018

(54) METHOD FOR PHOSGENATING COMPOUNDS CONTAINING HYDROXYL, THIOL, AMINO AND/OR FORMAMIDE GROUPS

(71) Applicant: BAYER AKTIENGESELLSCHAFT, Leverkusen (DE)

(72) Inventors: Leslaw Mleczko, Dormagen (DE); Aurel Wolf, Wuelfrath (DE); Ralf Schellen, Dormagen (DE); Konstantinos Metaxas, Cologne (DE); Jens Stefan Roggan, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 15/503,855

(22) PCT Filed: Aug. 17, 2015

(86) PCT No.: PCT/EP2015/068811
§ 371 (c)(1),
(2) Date: Feb. 14, 2017

(87) PCT Pub. No.: WO2016/026799
PCT Pub. Date: Feb. 25, 2016

(65) Prior Publication Data
US 2017/0274346 A1 Sep. 28, 2017

(30) Foreign Application Priority Data
Aug. 20, 2014 (DE) .......... 10 2014 111 902

(51) Int. Cl.
| | | |
|---|---|---|
| *C01B 7/01* | (2006.01) | |
| *B01D 71/06* | (2006.01) | |
| *B01J 19/18* | (2006.01) | |
| *B01J 31/02* | (2006.01) | |
| *C01B 32/80* | (2017.01) | |
| *C07C 263/10* | (2006.01) | |
| *C01F 7/02* | (2006.01) | |

(52) U.S. Cl.
CPC ....... *B01J 19/1893* (2013.01); *B01J 31/0231* (2013.01); *C01B 7/01* (2013.01); *C01B 32/80* (2017.08); *B01J 2523/31* (2013.01); *C01F 7/02* (2013.01); *C07C 263/10* (2013.01)

(58) Field of Classification Search
CPC .................................................. C01B 32/80
See application file for complete search history.

(56) References Cited

U.S. PATENT DOCUMENTS

| | | |
|---|---|---|
| 5,380,909 A | 1/1995 | Harley et al. |
| 6,932,951 B1 | 8/2005 | Losey et al. |
| 8,366,794 B2 | 2/2013 | Tremblay |
| 2008/0250700 A1* | 10/2008 | Tremblay ............ B01D 61/14 44/301 |

FOREIGN PATENT DOCUMENTS

| | | |
|---|---|---|
| CN | 101757859 A | 6/2010 |
| EP | 0 520 238 A1 | 12/1992 |
| WO | 2006-089429 A1 | 8/2006 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface (Year: 2005).*
Richter, V. Organic Chemistry of the Carbon Compounds, 1915, p. 430 (Year: 1915).*
Safe Work Australia, GHS Hazardous Chemical Information List, Aug. 2014, pp. 1-631 (Year: 2014).*
Mitchell et al. "Selection of Carbon Catalysts for the Industrial Manufacture of Phosgene", Catalysis Science & Technology (2012) vol. 2 pp. 2109-2115.
A.F. Ismail "A Review of the Latest Development of Carbon Membranes for Gas Separation" (2001) Journal of Membrane Science vol. 193, p. 1-18.
M. Reif "Porous, Catalytically Active Ceramic Membranes for Gas-Liquid Reactions: A Comparison Between Catalytic Diffuser and Forced Through Flow Concept" (2003) vol. 82, pp. 3-14.
International Search Report of PCT/EP2015/068811 dated Nov. 27, 2015.

* cited by examiner

*Primary Examiner* — Matthew P Coughlin
(74) *Attorney, Agent, or Firm* — McBee Moore Woodward & Vanik IP, LLC

(57) ABSTRACT

The invention relates to a method particularly for reacting phosgene with compounds that contain hydroxyl, thiol, amino and/or formamide groups, comprising the steps of: (I) providing a reactor which has a first reaction chamber (300, 310, 320, 330, 340, 350) and a second reaction chamber (200, 210, 220, 230, 240, 250, 260), the first and the second reaction chambers being separated from one another by means of a porous carbon membrane (100, 110, 120, 130, 140, 150); (II) providing carbon monoxide and chlorine in the first reaction chamber; and simultaneously (III) providing a compound containing hydroxyl, thiol, amino and/or formamide groups in the second reaction chamber. The porous carbon membrane is configured to catalyze the reaction of carbon monoxide and chlorine to obtain phosgene, and to allow this formed phosgene to pass into the second reaction chamber. The invention also relates to a reactor that is suitable for carrying out the claimed method.

15 Claims, 5 Drawing Sheets

METHOD FOR PHOSGENATING COMPOUNDS CONTAINING HYDROXYL, THIOL, AMINO AND/OR FORMAMIDE GROUPS

CROSS REFERENCE TO RELATED APPLICATIONS

This application is a § 371 National Stage Application of PCT/EP2015/068811, filed Aug. 17, 2015, which claims priority to German Application No. 10 2014 111 902.9 filed Aug. 20, 2014.

BACKGROUND

Field of the Invention

The studies that led to this invention were supported under Grant Agreement No. 245988-1 as part of the Seventh Framework Programme of the European Union (FP7/2007-2013)-INCAS (Integration of Nanoreactor and multisite Catalysis for a Sustainable chemical production).

DESCRIPTION OF RELATED ART

The present invention relates to a method of reaction of phosgene with compounds containing hydroxyl, thiol, amino and/or formamide groups, comprising the steps of: (I) providing a reactor comprising a first reaction space and a second reaction space, wherein the first and second reaction spaces are separated from one another by a porous carbon membrane; (II) providing carbon monoxide and chlorine in the first reaction space; and simultaneously (III) providing a compound containing hydroxyl, thiol, amino and/or formamide groups in the second reaction space. It further relates to a reactor suitable for performing the method of the invention.

Phosgene ($COCl_2$) is a key reagent in the production of pharmaceuticals, polyurethanes and polycarbonates. It is a very reactive but also very toxic chemical, and the industrial scale production process, because of the amounts of phosgene (hold-up) present in a plant, always harbors risks to the environment in the event of an unintended release resulting from leaks in pipelines or other damage to plant components.

One example of the industrial scale use of phosgene as key reagent is the preparation of diphenyl carbonate (DPC). DPC is an important intermediate for the synthesis of high-quality polycarbonates, for example through transesterification with bisphenol A. The synthesis of DPC proceeding from phenol and phosgene (direct phosgenation) proceeds in two steps: the first step comprises the preparation of phosgene in a gas phase reaction of carbon monoxide and chlorine, which typically occurs over activated carbon catalysts in a multitube fixed bed reactor. According to the boiling temperature of the cooling medium in the reactors, a distinction is made between phosgene preparation in cold combiners or hot combiners. By reaction of phenol with phosgene in the presence of a suitable catalyst, DPC is ultimately obtained. DPC preparation via direct phenol phosgenation, in comparison with the conventional interfacial methods (reaction of sodium phenoxide with phosgene), offers the advantage that the formation of large amounts of NaCl waste products is avoided.

Both the phosgene synthesis and the DPC synthesis are highly exothermic reactions with enthalpies of reaction of −107 and −54 kJ/mol. Particularly the exothermicity of the phosgene synthesis in the gas phase requires efficient cooling systems, but it is not possible to prevent hotspots in the reactor with local temperatures of more than 500° C. (cf. Mitchell et al., Catal. Sci. Technol., 2012). The occurrence of temperatures of more than 300° C. does not just lead to elevated material stress in the reactor but also adversely affects the equilibrium reaction of phosgene formation (the breakdown of phosgene predominates at more than 300° C.) and additionally increases the rate of deactivation of the catalyst, such that there is an overall drop in space-time yield and process efficient.

From the point of view of smaller hold-up volumes for improvement of process safety, microstructured reactors are of interest. For instance, U.S. Pat. No. 6,932,951 describes a microstructured reactor for the hydrogenation of cyclohexene to cyclohexane as an example application.

CN 101757859 A describes a carbon membrane reactor and a method for use thereof. It is a feature of the carbon membrane reactor that a defect-free carbon membrane is bonded to the housing of the reactor and a cavity is formed within the housing of the reactor, with the cavity that communicates with a charge orifice and an outlet orifice for coreactants forming a charge side and the cavity with an inlet and an outlet for purge gas communicates forming a passage side. The defect-free carbon membrane is filled with catalysts; alternatively, the catalysts are presented on the defect-free carbon membrane.

A review article on the topic of carbon membranes is "A review on the latest development of carbon membranes for gas separation", A. F. Ismail, L. I. B. David/Journal of Membrane Science 193 (2001) 1-18. A further publication is "Porous, catalytically active ceramic membranes for gas-liquid reactions: a comparison between catalytic diffuser and forced through flow concept", M. Reif, R. Dittmeyer, Catalysis Today 82 (2003) 3-14.

SUMMARY

Considering the present state of development, a demand for a method with the reduced phosgene hold-up is apparent. In the context of the invention, such a method is provided. More particularly, it was an object of the invention to provide a phosgenation method in which minimum amounts of free phosgene are present in the reaction system.

This object is achieved in accordance with the invention by a method of reacting a first compound with a second compound, wherein the first compound has a GHS hazard identification of GHS06 and is obtainable from the reaction of at least one first fluid precursor compound and a second fluid precursor compound and wherein the second compound is capable of a chemical reaction with the first compound, comprising the steps of:

(I) providing a reactor comprising a first reaction space and a second reaction space, wherein the first and second reaction spaces are separated from one another by a porous carbon membrane;

(II) providing the first and second precursor compounds in the first reaction space;

and simultaneously (III) providing the second compound in the second reaction space;

wherein the porous carbon membrane is set up to:

catalyze the reaction of the first and second precursor compounds to give the first compound and allow the first compound formed to move into the second reaction space.

DETAILED DESCRIPTION OF A PREFERRED EMBODIMENT

Figure 1:
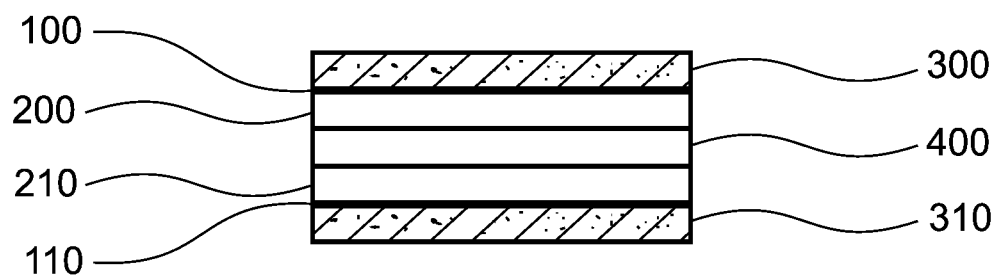
FIGS. 1-8 depict embodiments as described herein.

It is envisaged in accordance with the invention that the first compound has a hazard identification according to GHS (Globally Harmonized System of Classification, Labelling and Packaging of Chemicals of the United Nations) of GHS06. In the European Union, this is legislated for by Directive (EC) No. 1272/2008, also called CLP Regulation. The classification GHS06 refers to toxic or very toxic substances.

With regard to the first fluid precursor compound and the second fluid precursor compound, gases and liquids are envisaged in accordance with the invention, including solutions of solids in a solvent.

More particularly, the first compound may be phosgene, the first precursor compound may be carbon monoxide, the second precursor compound may be chlorine and the second compound may be a compound containing hydroxyl, thiol, amino and/or formamide groups.

Because of the major importance of the reaction of phosgene with a compound containing hydroxyl, thiol, amino and/or formamide groups, the present invention is elucidated in connection with this first and second compound, without being restricted thereto.

In the method of the invention, phosgene occurs only as a comparatively short-lived intermediate. The gas mixture of carbon monoxide and chlorine present in the first reaction space reacts on passage through the catalytically active carbon membrane to give phosgene. The phosgene formed in situ passes from the pores of the carbon membrane into the second reaction space, where it reacts with the compound containing hydroxyl, thiol, amino and/or formamide groups.

The method of the invention can avoid the presence of any great amounts of phosgene in the reaction system. A further advantage is the avoidance of local hotspots in the phosgene synthesis, as known from conventional plants. The compound containing hydroxyl, thiol, amino and/or formamide groups also serves to remove the heat of reaction. A low thickness of the membrane likewise promotes the removal of heat. In addition, the formation of NaCl as by-product is avoided with respect to the conventional phase transfer method. Overall, the integration of two reactions in one method results in an increase in the space-time yield of the method over a longer period and the thermal stress on the plant is reduced.

In step (I) of the method of the invention, a reactor is provided. The design of the reactor is not stipulated further at first and may, for example, be a tubular reactor for continuous operation or a tank reactor for a batchwise mode of operation. The reactor has two reaction spaces separated from one another by a porous carbon membrane. One reaction space is envisaged for the phosgene formation and one reaction space for the phosgenation. Through the choice of suitable liquid and gas pressures in the two reaction spaces, the passage of liquid reactants from the second reaction space into the first reaction space can be prevented.

The porous carbon membrane may be a self-supporting membrane or a membrane supported by a gas-permeable substrate. It can be obtained by pyrolysis of organic precursor compounds or else from carbon material produced beforehand, such as activated carbon, graphene or carbon nanotubes (CNTs). If the porosity of the membrane is suitable for the passage of phosgene, with the proviso of catalytic activity for the phosgene synthesis, carbon membranes from the industrial gas separation sector can be used.

The term "porous" in connection with the carbon membranes means here that pores connected to one another that are present in the membrane enable a path through the membrane at least for the phosgene molecules formed.

Steps (II) and (III) of the method of the invention are conducted simultaneously, in order that the phosgene formed in situ can react further very quickly. Examples of suitable compounds containing hydroxyl, thiol, amino and/or formamide groups are aromatic alcohols such as phenol, aliphatic alcohols, primary aromatic amines, secondary aromatic amines, primary aliphatic amines, secondary aliphatic amines, N,N-dimethylformamide and N-methylformanilide Especially aromatic and aliphatic alcohols and formamides are preferred; the former because of the use of the reaction products in polycarbonate production and the latter because of their use in Vilsmeier-Haack formylations. Preference is further given to primary amines, since they can be converted by phosgenation to the corresponding isocyanates which are used in polyurethane production.

Overall, the membrane can thus also be regarded as a pore reactor.

Corrosion-sensitive surfaces in the reactor can be protected, for example, by means of a stainless steel or $SiO_2$ coating.

With regard to the reaction conditions in the method of the invention, the reaction temperature for the phosgene synthesis may advantageously be between 80 and 300° C. and for the phosgenation (especially of phenol) between 150 and 300° C. Particular preference is given to a reaction temperature in the first and second reaction space of 190 to 210° C.

The pressure in the first and second reaction space may, for example, be 1 to 29 bar. Preference is given to a pressure of 24 to 26 bar. Especially within the preferred range, it is possible to reduce the residence time such that it is a few minutes (by contrast with one hour or more).

It is additionally advantageous in phosgenation reactions when the porous carbon membrane is also set up in order to prevent contact of $Cl_2$ with the starting materials and products in the second reaction space. In this way, it is possible to prevent the formation of chlorination products, for example chlorophenols.

Further embodiments and aspects of the present invention are elucidated hereinafter. They can be combined with one another as desired unless the opposite is apparent from the context.

In one embodiment of the method of the invention, the porous carbon membrane has a nominal pore size, determined by means of mercury porosimetry (ISO 15901-1), of ≥0.01 to ≤10 μm. The nominal pore size is understood as usual to mean the maximum of the pore size distribution. Preferred nominal pore sizes are ≥0.1 to ≤1.0 μm.

The membrane preferably in each case independently has the following further properties:
Thickness: ≥1 to ≤10 mm
Specific surface area (BET): ≥100 to ≤2000 $m^2/g$
Porosity: ≥0.1 to ≤0.5
Tortuosity: ≥1 to ≤15
Thermal conductivity: ≥1 to ≤175 W/m/K
Membrane loading in the reactor: ≥300 to ≤800 $kg/m^3$ In a further embodiment of the method of the invention, the porous carbon membrane further comprises a catalyst for the reaction of the first compound (preferably of phosgene) with the second compound (preferably the compound containing hydroxyl, thiol, amino and/or formamide groups), arranged at least partly on the side of the porous carbon membrane facing the second reaction space. Appropriately, the catalyst is a heterogeneous catalyst. In the case of the phosgenation of aromatic alcohols such as phenol, it is possible to use $Al_2O_3$, for example.

In a further embodiment of the method of the invention, a homogeneous catalyst is additionally present in the second reaction space. The catalyst, preferably for the reaction of phosgene with the compound containing hydroxyl, thiol, amino and/or formamide groups, is thus dissolved in the reaction medium present in the second reaction space. In the case of the phosgenation of aromatic alcohols such as phenol, it is possible to use $TiCl_4$ or pyridine, for example.

In a further embodiment of the method of the invention, an open-cell foam is additionally present in the first reaction space. In principle, suitable foam materials are all of those that are stable at the temperatures that exist in the phosgene synthesis and especially up to 300° C. The foam is preferably a metal or ceramic foam. As well as better mixing of the CO and $Cl_2$ reactants, a foam additionally has the property that the first reaction space can be mechanically supported thereby. This is advantageous especially in multilayer reactors.

In a further embodiment of the method of the invention, the reactor further comprises a cavity to accommodate a heat transfer fluid. In this way, it is possible to implement heat exchangers, especially crossflow heat exchangers. Heat transfer fluids used may be liquids such as water or oil or else gases such as air.

In a further embodiment of the method of the invention, the reactor further comprises a dwell zone to complete the reaction of the first compound (preferably phosgene) with the second compound (preferably with the compound containing hydroxyl, thiol, amino and/or formamide groups). Specifically in the case of multistage reactions in which, for example, the reaction of phenol with phosgene to give the chloroformate formed as an intermediate proceeds quickly but the further reaction of the chloroformate with phenol to give DPC proceeds more slowly, a dwell zone can result in an increase in the yield of the reaction in the second reaction space in flow direction after the phosgene synthesis (such that no additional phosgene moves into the second reaction space).

In a further embodiment of the method of the invention, the compound containing hydroxyl, thiol, amino and/or formamide groups is phenol, dimethylformamide or N-methylformanilide.

In a further embodiment of the method of the invention, the reactor comprises a multitude of first reaction spaces, second reaction spaces and porous carbon membranes, wherein one first and one second reaction space are separated from one another in each case by a porous carbon membrane. It is thus possible to obtain flat, multilayer and modular membrane reactors.

In a further embodiment of the method of the invention, the reactor has a cylindrical construction with first reaction space and second reaction spaces arranged concentrically from the inside outward, wherein the first and second reaction spaces are separated from one another by the porous carbon membrane. In that case, the reactor behaves in principle like a bubble column reactor. Preferably, two or more of these reactors are combined to form a shell and tube reactor.

The individual cylindrical reactor may independently have the following properties:
Diameter of the second reaction space: $\geq 3$ to $\leq 10$ cm
Length of the second reaction space: $\geq 3$ to $\leq 20$ m
Dwell time of the reaction mixture in the second reaction space: $\geq 1$ to $\leq 60$ minutes
Molar excess of phenol: $\geq 4$ to $\leq 6$ In a further embodiment of the method of the invention, the first reaction space and/or the second reaction space have a cross-sectional area at right angles to the flow direction of the fluid flowing through of $\geq 8\cdot 10^{-5}$ to $\leq 8\cdot 10^{-4}$ m$^2$. Preferably, the cross-sectional area is $\geq 1\cdot 10^{-4}$ to $\leq 7\cdot 10^{-4}$ m$^2$ and more preferably $\geq 2\cdot 10^{-4}$ to $\leq 6\cdot 10^{-4}$ m$^2$.

In a further embodiment of the method of the invention, the reactor comprises a multitude of first reaction spaces surrounded by a common second reaction space.

As well as the planar design, preference is given to a form of the carbon membrane in which it takes the form of a hollow cylinder closed at one end.

The invention further relates to a reactor for reaction of phosgene with compounds containing hydroxyl, thiol, amino and/or formamide groups, comprising:
a first reaction space and a second reaction space, wherein the first and second reaction spaces are separated from one another by a porous carbon membrane; and
a catalyst for the reaction of phosgene with the compound containing hydroxyl, thiol, amino and/or formamide groups, arranged at least partly on the side of the porous carbon membrane facing the second reaction space.

Appropriately, the catalyst is a heterogeneous catalyst. In the case of the phosgenation of aromatic alcohols such as phenol, it is possible to use $Al_2O_3$, for example In one embodiment of the reactor of the invention, an open-cell foam is additionally present in the first reaction space. In principle, suitable foam materials are all of those that are stable at the temperatures that exist in the phenol synthesis and especially up to 300° C. The foam is preferably a metal or ceramic foam. As well as better mixing of the CO and $Cl_2$ reactants, a foam has the further property that the first reaction space can be mechanically supported. This is advantageous especially in multilayer reactors.

In a further embodiment of the reactor of the invention, the first reaction space and/or the second reaction space have a cross-sectional area at right angles to the flow direction of the fluid flowing through of $\geq 8\cdot 10^{-5}$ to $\leq 8\cdot 10^{-4}$ m$^2$.

In a further embodiment of the reactor of the invention, the porous carbon membrane has a nominal pore size, determined by means of mercury porosimetry (ISO 15901-1), of $\geq 0.01$ to $\leq 10$ μm. The nominal pore size is understood as usual to mean the maximum of the pore size distribution. Preferred nominal pore sizes are $\geq 0.1$ to $\leq 1$ μm.

The membrane preferably in each case independently has the following further properties:
Thickness: $\geq 1$ to $\leq 10$ mm
Specific surface area (BET): $\geq 100$ to $\leq 2000$ m$^2$/g
Porosity: $\geq 0.1$ to $\leq 0.5$
Tortuosity: $\geq 1$ to $\leq 15$
Thermal conductivity: $\geq 1$ to $\leq 175$ W/m/K
Membrane loading in the reactor: $\geq 300$ to $\leq 800$ kg/m$^3$ In a further embodiment of the reactor of the invention, the reactor further comprises a cavity to accommodate a heat transfer fluid. It is thus possible to implement heat exchangers, especially crossflow heat exchangers. Heat transfer fluids used may be liquids such as water or oil or else gases such as air.

In a further embodiment of the reactor of the invention, the reactor further comprises a dwell zone to complete the reaction of phosgene with the compound containing hydroxyl, thiol, amino and/or formamide groups. Specifically in the case of multistage reactions in which, for example, the reaction of phenol with phosgene to give the chloroformate proceeds quickly but the reaction of the chloroformate with phenol to give DPC proceeds more slowly, a dwell zone can result in destruction of phosgene in the second reaction space in flow direction after the phosgene synthesis (such that no additional phosgene moves into the second reaction space).

In a further embodiment of the reactor of the invention, the reactor comprises a multitude of first reaction spaces, second reaction spaces and porous carbon membranes, wherein one first and one second reaction space are separated from one another in each case by a porous carbon membrane. It is thus possible to obtain flat, multilayer and modular membrane reactors.

In a further embodiment of the reactor of the invention, the reactor has a cylindrical construction with first reaction space and second reaction space arranged concentrically from the inside outward, wherein the first and second reaction spaces are separated from one another by the porous carbon membrane. In that case, the reactor behaves in principle like a bubble column reactor.

Preferably, two or more of these reactors are combined to form a shell and tube reactor.

The individual cylindrical reactor may independently have the following properties:

Diameter of the second reaction space: ≥3 to ≤10 cm
Length of the second reaction space: ≥3 to ≤20 m In a further embodiment of the reactor of the invention, the first reaction space and/or the second reaction space have a cross-sectional area at right angles to the flow direction of the fluid flowing through of $\geq 8 \cdot 10^{-5}$ to $\leq 8 \cdot 10^{-4}$ m$^2$.

In a further embodiment of the reactor of the invention, the reactor comprises a multitude of first reaction spaces surrounded by a common second reaction space.

The present invention is illustrated in detail by the figures which follow, but without being restricted thereto. The figures show:

FIG. 1 a cross section through a reactor for the method of the invention

Figure 2:
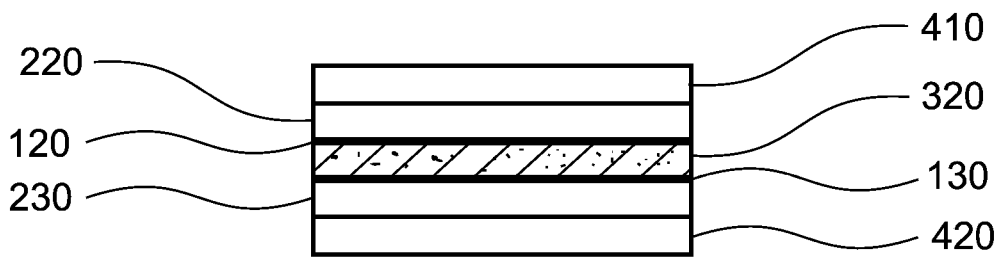
Figure 3:
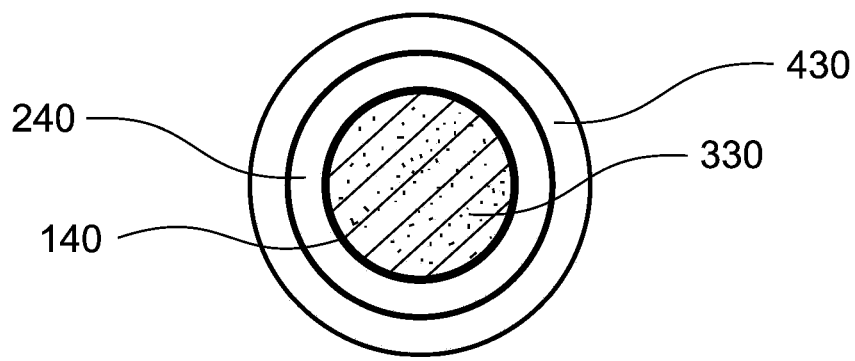
Figure 4:
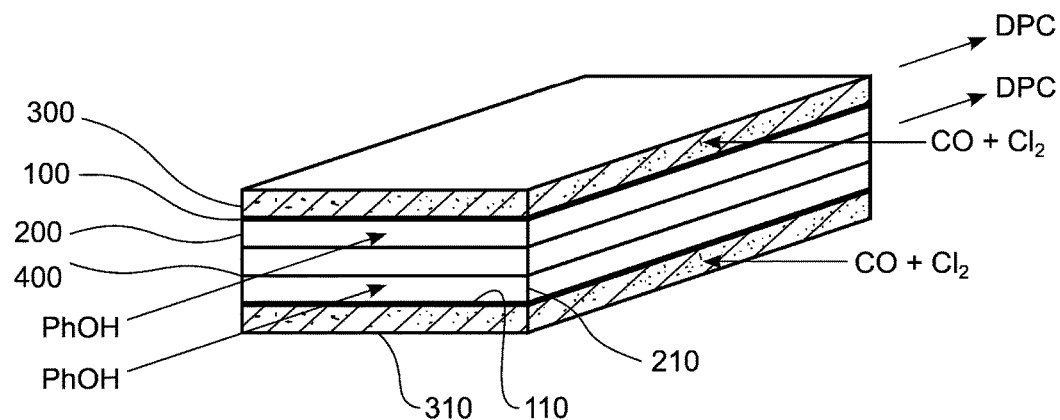
Figure 5:
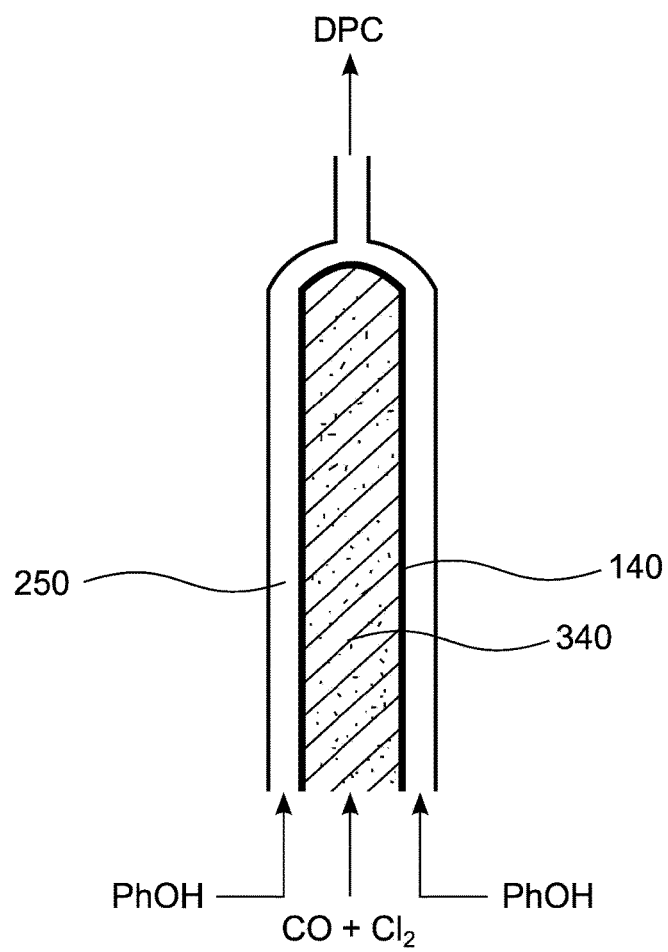
Figure 6:
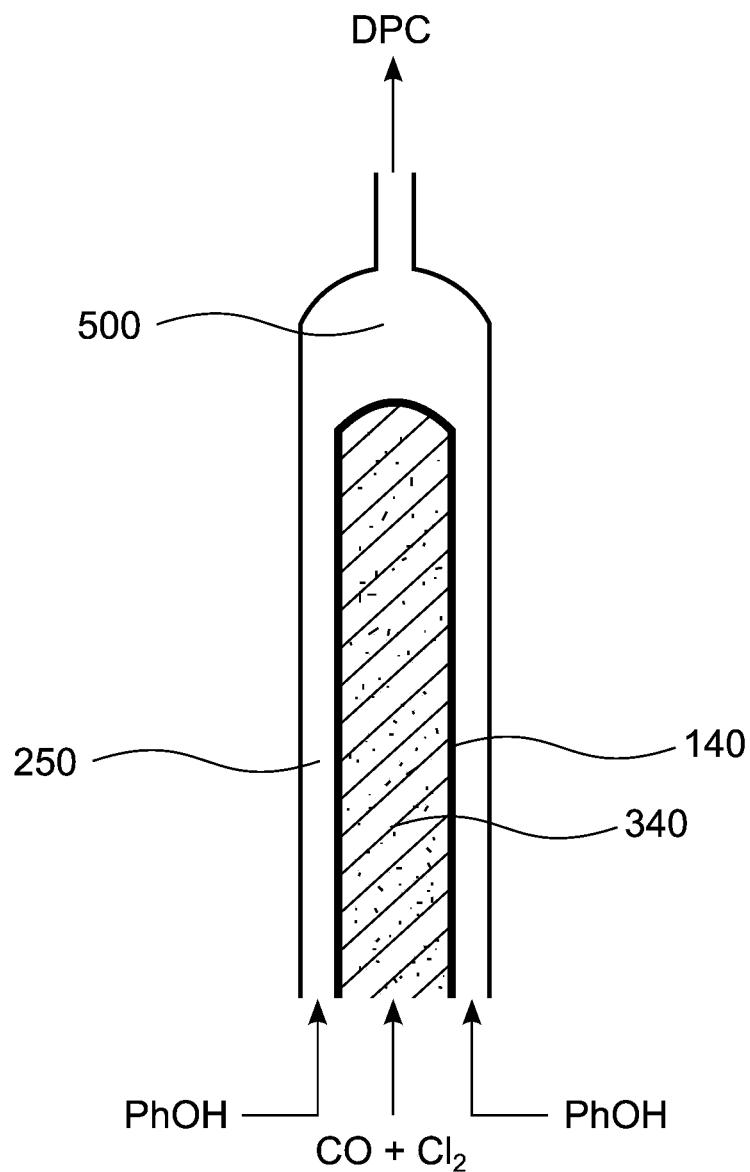
Figure 7:
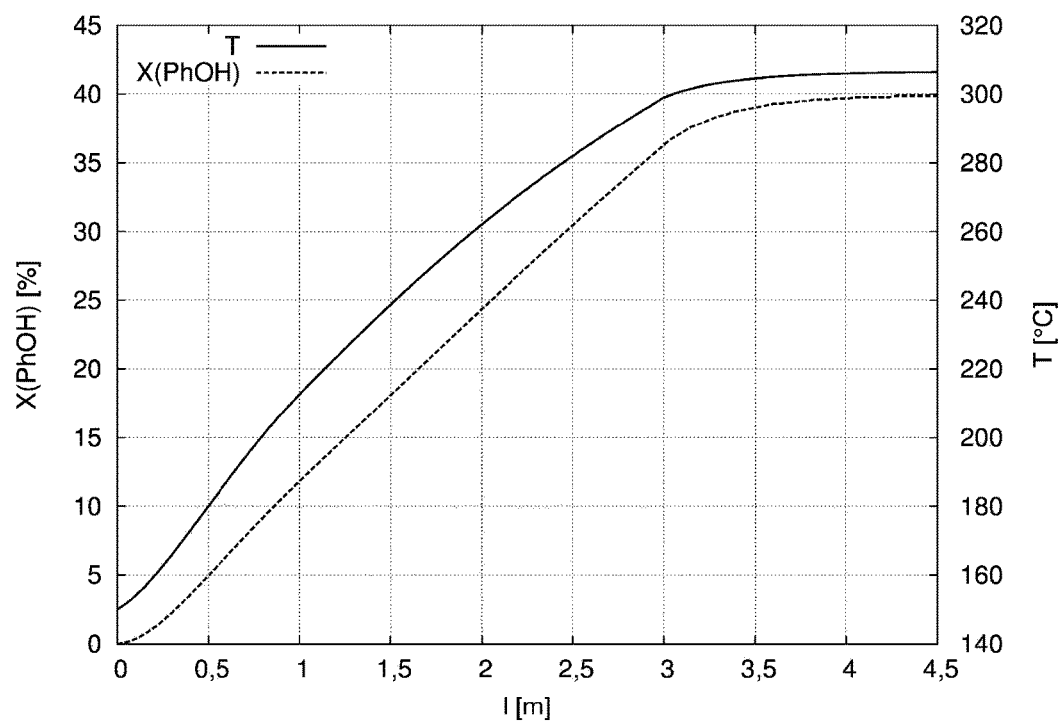
Figure 8:
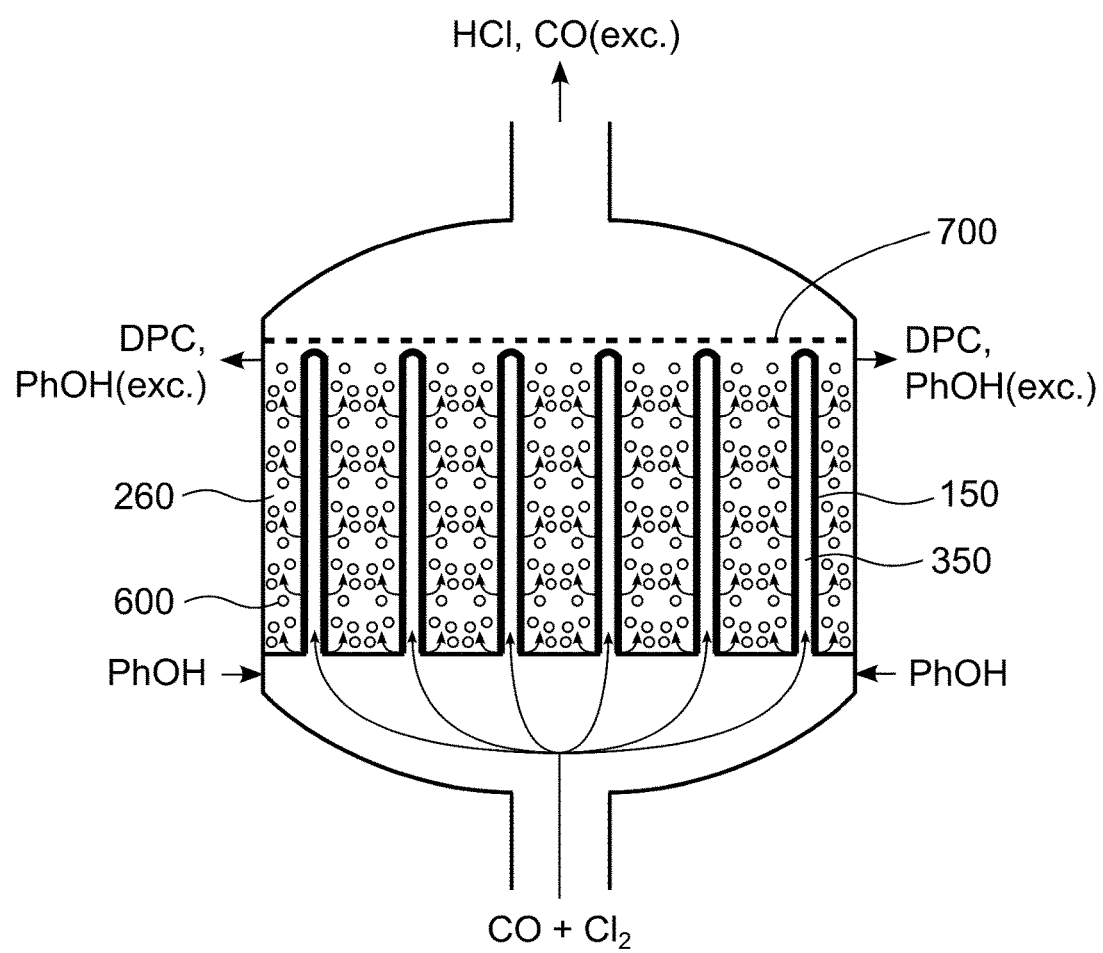

FIG. 2 a cross section through a further reactor for the method of the invention FIG. 3 a cross section through a further reactor for the method of the invention FIG. 4 a cross section through a further reactor for the method of the invention FIG. 5 a cross section through a further reactor for the method of the invention FIG. 6 a cross section through a further reactor for the method of the invention FIG. 7 simulation results for a method of the invention FIG. 8 a cross section through a further reactor for the method of the invention FIG. 1 shows a schematic cross section through a reactor as usable in the method of the invention. Two porous carbon membranes 100, 110 each separate a first reaction space 300, 310 from second reaction spaces 200, 210. Arranged centrally is a further cavity 400 through which a heat transfer fluid can flow, such that the cavity 400 can assume the function of a heat exchanger. The first reaction spaces 300, 310 contain an open-pore foam which, as well as a supporting function, also brings about better gas mixing. This may, for example, be an open-pore metal foam. Carbon monoxide and chlorine are introduced into the first reaction spaces 300, 310 and react under catalysis by the membranes 100, 110 to give phosgene. This phosgene passes through the pores of the membranes 100, 110 into the second reaction spaces 200, 210. In the second reaction spaces 200, 210, a compound containing hydroxyl, thiol, amino and/or formamide groups, such as phenol, is present, and reacts with the phosgene. To promote this reaction, a catalyst may be used. This may take the form of a homogeneous catalyst in second reaction spaces 200, 210. Alternatively or additionally, a heterogeneous catalyst may be present on the side of the membranes 100, 110 facing the second reaction spaces 200, 210.

FIG. 2 shows a schematic cross section through a further reactor as usable in the method of the invention. The reactor shown here differs from the reactor according to FIG. 1 by the central arrangement of the first reaction space 320 which is delimited from second reaction spaces 220, 230 at the top and bottom by porous carbon membranes 120, 130. Arranged adjoining the second reaction spaces 220, 230 are cavities 410, 420 to accommodate a heat transfer fluid. The reactor shown in FIG. 2 is advantageous when a greater amount of heat of reaction has to be removed compared to the reactor from FIG. 1.

FIG. 3 shows a schematic cross section through a further reactor as usable in the method of the invention. The reactor has a concentric design, and so it is possible to implement a tubular reactor or shell and tube reactor. The view shown here is a cross section at right angles to the main axis of the reactor. On the inside is the first reaction space 330 with an open-pore foam as already described above. The porous carbon membrane 140 separates the first reaction space 330 from the second reaction space 240. Cavity 430 again serves to accommodate a heat transfer fluid.

FIG. 4 shows a schematic cross section through a further reactor as usable in the method of the invention. The reactor is as described in FIG. 1. DPC synthesis is to be elucidated here by way of example CO gas and Cl$_2$ gas are introduced into the first reaction spaces 300, 310 and form phosgene on passage through the catalytically active carbon membrane 100, 110. On entry into the second reaction spaces 200, 210, the phosgene formed in the membrane 100, 110 reacts with phenol (PhOH) via the chloroformate intermediate to give diphenyl carbonate (DPC). The streams of phenol and of CO and Cl$_2$ run orthogonally to one another. Appropriately, a heat transfer fluid flows through the cavity 400, likewise orthogonally to the flow direction of the phenol and counter to the CO and Cl$_2$ stream. In that case, it is possible to implement a crossflow heat exchanger.

FIG. 5 shows a schematic cross section through a further reactor as usable in the method of the invention. This is a tubular reactor which may likewise be part of a shell and tube reactor. CO gas and Cl$_2$ gas are introduced into the first reaction space 340 and react on passage through the catalytically active, porous carbon membrane 140 to form phosgene. On entry of phosgene into the second reaction space 250, it reacts, for example, with phenol to give diphenyl carbonate, with intermediate formation of the chloroformate intermediate. The reaction product leaves the tubular reactor at the upper end. In the case of the tubular reactors or shell and tube reactors, direct cooling from the outside is possible by means of a free-flowing heat transfer medium, such that a separate cavity as in the reactors outlined above is dispensable.

In the arrangement shown in FIG. 6, the difference from the reactor according to FIG. 5 is that, in the second reaction space 250, in a dwell zone 500 present downstream of the porous carbon membrane 150 viewed in flow direction of the phenol, the reaction that proceeds in the second reaction space 250 can progress further. Thus, if required, the overall conversion of the reaction can be increased further.

FIG. 7 shows simulation results for a method of the invention. The synthesis of DPC by phosgenation of phenol was modeled on the basis of known kinetic information. Kinetics for homogeneous and heterogeneous catalyses were introduced into the model from in-house results. The physical properties were taken from the Aspen Properties® software package and, where possible, compared with the experimental Detherm database. The specifications employed were: 99.9% conversion of $Cl_2$ in the phosgene synthesis, 100% conversion of the phosgene in the phosgenation of phenol (no phosgene at the reactor outlet), maximum temperature 300° C. at the membrane. The pressure used was 25 bar, in order to effectively dissolve phosgene in the liquid phenol and therefore to significantly reduce the lifetime thereof. The molar ratio of phenol to phosgene required for 100% phosgene conversion and for cooling of the reactor was ≥4:1. The reactor used for the modeling corresponds to the setup shown in FIG. 6 and therefore had a dwell zone 500. In FIG. 7, the phenol conversion X(PhOH) and the temperature at the porous carbon membrane T are plotted against the length of the tubular reactor. The reactor had a total length of 4.5 meters. The section from 3 meters onward corresponds to the dwell zone for full phosgene conversion; the actual phosgene synthesis proceeds in the first 3 meters of the reactor. The starting temperature of the phenol was 140° C.

An annual production of DPC of about 20 000 metric tonnes can be achieved according to the above model calculation in a shell and tube reactor with about 400 reactors according to FIG. 6.

FIG. 8 shows a schematic cross section through a further reactor for the method of the invention. As can be seen, a multitude of first reaction spaces 350 open at one end are present, separated by membranes 150 from a common second reaction space 260. At the lower end of the reactor, CO and chlorine gas are introduced. The gas mixture passes into the first reaction spaces and reacts under catalysis by the membranes to give phosgene, which passes through the membranes. This is shown schematically by arrows and the gas bubbles 600. At the lower end of the second reaction space, phenol is introduced. This is in the liquid phase, for example in molten form or in solution. The surface of the liquid phase in the second reaction space is shown by the dotted line 700. Accordingly, a gas phase is present above the liquid phase. In the second reaction space, the phenol introduced reacts with the phosgene that has passed through the membranes to give DPC. The product mixture of DPC and unconverted phenol ("PhOH(exc.)") is withdrawn at the upper end of the second reaction space. At the upper end of the reactor, HCl as gaseous product and unconverted CO ("CO(exc.)") are discharged.

An annual production of DPC of about 20 000 metric tonnes can be achieved according to the aforementioned model calculation in a reactor with about 400 first reaction spaces according to FIG. 8.

The invention claimed is:

1. A method of reacting a first compound with a second compound,
    wherein the first compound has a GHS hazard identification of GHS06 and is obtainable from the reaction of at least one first fluid precursor compound and a second fluid precursor compound and
    wherein the second compound is capable of a chemical reaction with the first compound, said method comprising:
    (I) providing a reactor comprising a first reaction space and a second reaction space,
        wherein the first and second reaction spaces are separated from one another by a porous carbon membrane;
    (II) providing the first and second fluid precursor compounds in the first reaction space; and simultaneously
    (III) providing the second compound in the second reaction space;
        wherein the porous carbon membrane is set up to:
            catalyze the reaction of the first and second fluid precursor compounds to give the first compound and
            allow the first compound formed to move into the second reaction space,
        wherein the first compound is phosgene, the first fluid precursor compound is carbon monoxide, the second fluid precursor compound is chlorine and the second compound is a compound containing one or more hydroxyl, thiol, amino and/or formamide groups.

2. The method as claimed in claim 1, wherein the porous carbon membrane has a nominal pore size, determined by mercury porosimetry using ISO 15901-1, of ≥0.01 to ≤10 μm.

3. The method as claimed in claim 1, wherein the porous carbon membrane further comprises a catalyst for reaction of the first compound with the second compound, arranged at least partly on a side of the porous carbon membrane facing the second reaction space.

4. The method as claimed in claim 1, wherein a homogeneous catalyst is additionally present in the second reaction space.

5. The method as claimed in claim 1, wherein an open-cell foam is additionally present in the first reaction space.

6. The method as claimed in claim 1, wherein the reactor further comprises a cavity to accommodate a heat transfer fluid.

7. The method as claimed in claim 1, wherein the reactor additionally comprises a dwell zone to complete the reaction of the first compound with the second compound.

8. The method as claimed in claim 1, wherein the reactor comprises a multitude of first reaction spaces, second reaction spaces and porous carbon membranes, wherein one first and one second reaction space are separated from one another in each case by a porous carbon membrane.

9. The method as claimed in claim 1, wherein the reactor has a cylindrical construction with the first reaction space and the second reaction space arranged concentrically from the inside outward, wherein the first and second reaction spaces are separated from one another by the porous carbon membrane.

10. The method as claimed in claim 1, wherein the reactor is a flow reactor and wherein the first reaction space and/or the second reaction space have a cross-sectional area at right angles to the flow direction of the fluid flowing through of ≥8·10$^{-5}$ to ≤8·10$^{-4}$ m$^2$.

11. The method as claimed in claim 1, wherein the reactor comprises a multitude of first reaction spaces surrounded by a common second reaction space.

12. The method as claimed in claim 1, where the second compound is a compound containing one or more hydroxyl groups.

13. The method as claimed in claim 1, where the second compound is a compound containing one or more thiol groups.

14. The method as claimed in claim 1, where the second compound is a compound containing one or more amino groups.

15. The method as claimed in claim 1, where the second compound is a compound containing one or more formamide groups.

\* \* \* \* \*

UNITED STATES PATENT AND TRADEMARK OFFICE
CERTIFICATE OF CORRECTION

PATENT NO. : 10,105,675 B2
APPLICATION NO. : 15/503855
DATED : October 23, 2018
INVENTOR(S) : Leslaw Mleczko et al.

Page 1 of 1

It is certified that error appears in the above-identified patent and that said Letters Patent is hereby corrected as shown below:

On the Title Page

(72) Inventors should read: LESLAW MLECZKO, DORMAGEN (DE); AUREL WOLF, WUELFRATH (DE); RALPH SCHELLEN, DORMAGEN (DE); KONSTANTINOS METAXAS, KOELN (DE); JENS STEFAN ROGGAN, KOELN (DE)

Signed and Sealed this
Twenty-ninth Day of January, 2019

Andrei Iancu
*Director of the United States Patent and Trademark Office*